US00PP15066P2

(12) United States Plant Patent
Carruth

(10) Patent No.: US PP15,066 P2
(45) Date of Patent: Aug. 3, 2004

(54) MINIATURE ROSE PLANT NAMED 'WEKSACTRUMI'

(50) Latin Name: *Rosa hybrida*
Varietal Denomination: WEKsactrumi

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/687,058

(22) Filed: Oct. 15, 2003

(51) Int. Cl.[7] ..... A01H 5/00
(52) U.S. Cl. ..... Plt./122
(58) Field of Search ..... Plt./122

*Primary Examiner*—Anne Marie Grunberg
*Assistant Examiner*—Susan B. McCormick-Ewoldt
(74) *Attorney, Agent, or Firm*—Christie, Parker & Hale, LLP

(57) ABSTRACT

A new variety of Miniature rose suitable for garden decoration, having flowers of cherry red coloration.

1 Drawing Sheet

Classification: The present invention relates to a new *Rosa hybrida* plant.

Variety denomination: The new plant has the varietal denomination 'WEKsactrumi'.

BACKGROUND OF THE INVENTION

This invention relates to a new and distinct variety of Miniature Rose. It has as its seed parent the variety known as 'POUlclaus' (U.S. Plant Pat. No. 9,063) and as its pollen parent an undisseminated seedling of my creation.

SUMMARY OF THE INVENTION

Among the features which distinguish the new variety from other presently available and commercial rose cultivars known to the inventor are the following combination of characteristics: its moderately mucronate to round petal apices, its excellent color stability throughout the life of the flower, its red suffusion on the inside of the sepals, its very smooth rachis and its very low thorned shoots and branches. The plant has a bushy moderately spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKsactrumi' may be asexually propagated by cuttings, budding and grafting. The budding and grafting successfully occurred on the plant/rootstock *Rosa hybrida* cv. 'Dr. Huey'.

COMPARISON WITH PARENTS

The new rose may be distinguished from its seed parent, 'POUlclaus' by the following combination of characteristics: whereas 'WEKsactrumi' bears flowers of cherry red coloration with double petalage (about 21 to 32 petals), 'POUlclaus' bears flowers of deeper red coloration with significantly lesser petalage (about 14 to 18 petals). The seed parent bears several large prickles and few small prickles on its branches and new shoots, whereas 'WEKsactrumi' bears no large or small prickles on the branches or the new shoots.

The new rose may be distinguished from its pollen parent, an undisseminated seedling of my creation by the following combination of characteristics: whereas 'WEKsactrumi' bears medium size flowers (about 4 to about 5 cm. in diameter) of cherry red coloration, the undisseminated seedling bears significantly smaller flowers of orange-red coloration. 'WEKsactrumi' has a bushy moderately spreading medium height growth habit, whereas the pollen parent has a very compact and significantly shorter mature growth habit.

BRIEF DESCRIPTION OF THE ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of September. Phenotypic expression may vary with environmental, cultural and climatic conditions, as well as differences in conditions of light and soil.

FLOWER

The new variety sometimes bears its flowers singly, usually in clusters of three to ten or more per stem. Flowers may be borne in regular rounded clusters on strong medium to long stems (about 13 to about 56 cm.). Outdoors, the plant blooms abundantly and nearly continuously during the growing season. The flowers have a slight tea fragrance.

BUD

The peduncle is about 1.6 to about 4.1 cm. in length, of average to heavy caliper (about 0.2 to about 0.3 cm. in diameter), and usually erect. It is moderately smooth, with many stipitate glands and very few hairs. Peduncle color is between 144A and 146B often heavily suffused, especially on the side exposed to the sun, with between 187A and 183A.

Before the calyx breaks, the bud is about 0.7 to about 1.2 cm. in diameter at the widest point, about 1.2 to about 1.8 cm. in length, and pointed to somewhat ovoid in shape. The surface of the bud bears few foliaceous appendages and very few stipitate glands, usually with slender entire foliaceous parts extending beyond the tip of the bud about ½ or more of its length. Bud color is between 144A and 146B often heavily suffused, especially on the side exposed to the sun, with between 187A and 183A.

The sepals are about 1.6 to about 2.5 cm. in length and about 0.4 to about 0.7 cm. in width at the widest point. The outer surface color of the sepal is between 144A and 146B often heavily suffused, especially on the side exposed to the sun, with between 187A and 183A. The inner surface color of the sepal is between 138A and 139D. After the sepals open, the inner surface color is sometimes heavily suffused, especially on the area exposed to the sun, with between 187A and 187B. The inner surface is covered with fine wooly tomentum; sepal margins are lined with many stipitate glands.

As the petals open (after the calyx breaks), the bud is about 1.1 to about 1.6 cm. in diameter at the widest point, about 1.6 to about 2.2 cm. in length, and moderately ovoid to somewhat pointed in form. The color of the under surfaces of the newly opened petals is between 53A and 53C. At the point where the petal attaches, there is a very small zone of between 1D and 2D. The color of the upper surfaces of the newly opened petals is between 53A and 46A. At the point where the petal attaches, there is a very small zone of between 1D and 2D.

BLOOM

When fully open, the bloom ranges from about 4 to about 5 cm. in diameter. Petalage is double with about 21 to 32 petals and about 6 to 10 petaloids irregularly arranged. When partially open, the bloom form is moderately globular to cupped, and the petals are somewhat tightly spiraled to cupped with petal edges somewhat reflexed outward. When fully open, the bloom form is somewhat flat to slightly cupped, and the petals are loosely cupped with petal edges moderately reflexed outward.

PETALS

The substance of the petals is moderately heavy and of somewhat thin thickness, with upper surfaces moderately satiny to somewhat velvety and under surfaces mostly matte to somewhat shiny. The outer petals are nearly round to somewhat obovate in shape with apices moderately mucronate to round. The inner petals are broadly obovate in shape with apices mostly round but sometimes slightly mucronate. The petals are about 1.1 to about 2.4 cm. in length and about 0.5 to about 2.4 cm. in width at the widest point. Petal margins are entire.

NEWLY OPENED FLOWER

The under surface color of the outer and intermediate petals is between 60A and 53C. At the point where the petal attaches, there is a very small zone of between 4D and 155A. The upper surface color of the outer and intermediate petals is between 53B and 46A. At the point when the petal attaches, there is a very small zone of between 4D and 155A.

The under surface color of the inner petals is between 53B and 53C. The upper surface color of the inner petals is between 53A and 46A.

The general tonality of the newly opened flower is between 53B and 46A.

THREE-DAY-OLD FLOWER

The under surface color of the outer, intermediate and inner petals is between 60A and 53C. At the point where the petal attaches, there is a very small zone of between 4D and 155A.

The upper surface color of the outer, intermediate and inner petals is between 64C and 67C at the base of the petal that gradually suffuses to between 53B and 46A near the center of the petal and is often moderately overlaid near the very tip of the petals with a wash of between 187B and 187A. At the point where the petal attaches, there is a very small zone of between 4D and 155A.

The general tonality of the three-day-old flower is between 64C and 67C at the base of the petal that gradually suffuses to between 53B and 46A near the center of the petal and is often moderately overlaid near the very tip of the petals with a wash of between 187B and 187A.

On the spent bloom, the petals usually drop off cleanly.

In September in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 80) and are arranged regularly about the pistils; a few are mixed with petaloids. The filaments are of very short length (about 0.2 to about 0.5 cm.), most with anthers. Filaments are between 6C and 5B in color. The anthers are somewhat large for the class and all open approximately at the same time. Anther color is between 19A and 39B when immature and between 164D and 175B at maturity. Pollen is very sparse.

FEMALE REPRODUCTIVE ORGANS

Pistils vary in number (average about 35). The styles are moderately even, moderately short in length (about 0.3 to about 0.5 cm.), very thin in caliper, and moderately separated to somewhat columnar. Stigma color is between 11D and 8D. Style color is between 154D and 1D often heavily suffused near the top with between 53C and 53D. Ovaries are usually all enclosed in the calyx.

Hips have not been observed on this variety when grown in Upland, Calif.

FOLIAGE

The compound leaves are usually comprised of three to five or more leaflets and are borne abundantly. The five-leaflet leaves are about 7.1 to about 9.8 cm. in length and about 5.2 to 6.2 cm. in width at the widest point, moderately leathery in texture, and semi-glossy in finish. The terminal leaflets are about 2.7 to about 4.4 cm. in length and about 1.6 to about 2.4 cm. in width at the widest point, shaped moderately oval to somewhat ovate with acute apices and rounded to somewhat acute bases. Their margins are usually simply serrate.

The upper surface color of the mature leaf is between 147A and 137C. The under surface color of the mature leaf is between 147B and 138B. The upper surface color of the young leaf is between 146A and 144A, sometimes heavily suffused with between 187A and 183B. The under surface color of the young leaf is between 147B and 138B, sometimes lightly suffused with between 187B and 183B.

The rachis is average in caliper and very smooth. The upper side is shallowly grooved with some hairs and stipitate glands on the edges of the grooves. The under side of the rachis is very smooth without any hairs or stipitate glands. The rachis color is between 144B and 146D sometimes suffused, especially on the young leaves, with between 187B and 183B.

The stipules are about 1.0 to about 1.6 cm. in length and very wide (about 0.4 to about 0.7 cm.) with long straight points that usually turn out at an angle of more than 45 degrees. The stipules color is between 137A and 145B sometimes suffused, especially on the young leaves, with between 187B and 183B.

The petiole is about 0.3 to about 1.1 cm. in length and about 0.1 to about 0.15 cm in diameter at the widest point. The petiole color is between 144B and 146D sometimes suffused, especially on the young leaves, with between 187B and 183B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy moderately spreading medium height growing habit (about 60 to about 77 cm. in height and about 100 to about 120 cm. spread at the widest point), with very full branching. It displays moderately vigorous growth and the canes are of somewhat heavy caliper for the class.

The color of the major stems is between 146A and 146B. They bear very few large prickles that are about 0.5 to about 0.8 cm. in length. The large prickles are almost straight and angled slightly downward with a moderately short length broad rounded to somewhat oval base; prickle color is between 201C and 174B. The major stem bears no small prickles.

The color of the branches is between 146B and 137C. They bear no large or small prickles.

The color of the new shoots is between 144A and 143A sometimes heavily suffused with between 187A and 183B. They bear no large or small prickles.

I claim:

1. A new and distinct Miniature rose plant of the variety substantially as described and illustrated herein.

* * * * *

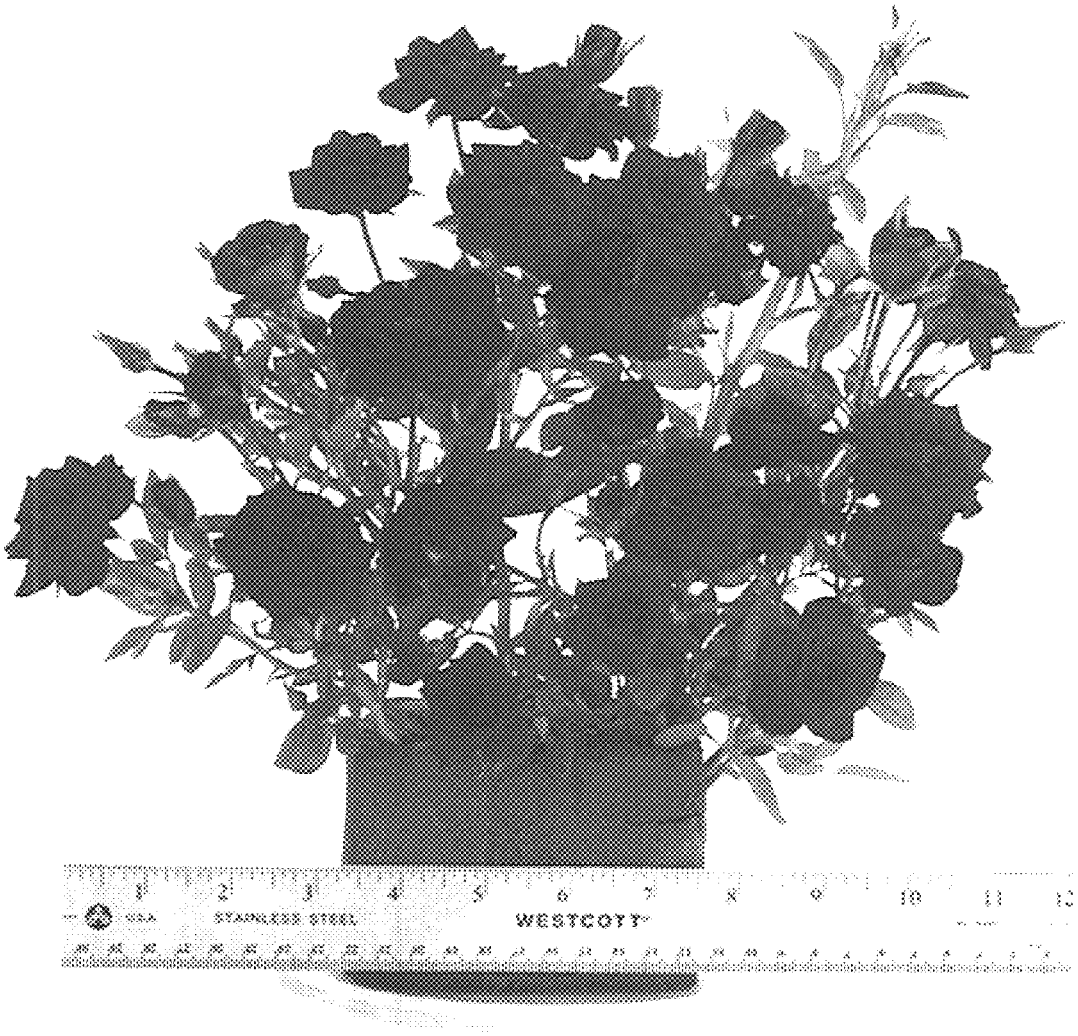
STAINLESS STEEL
WESTCOTT